United States Patent
Kawai et al.

(10) Patent No.: US 11,399,988 B2
(45) Date of Patent: Aug. 2, 2022

(54) WIRELESS COMMUNICATION DEVICE, DIAPER AND MOISTURE DETECTING SYSTEM

(71) Applicant: TORAY INDUSTRIES, INC., Tokyo (JP)

(72) Inventors: Shota Kawai, Shiga (JP); Yoshihiro Kariya, Shiga (JP); Junji Wakita, Tokyo (JP); Seiichiro Murase, Shiga (JP)

(73) Assignee: TORAY INDUSTRIES, INC., Tokyo (JP)

( * ) Notice: Subject to any disclaimer, the term of this patent is extended or adjusted under 35 U.S.C. 154(b) by 323 days.

(21) Appl. No.: 16/645,683

(22) PCT Filed: Aug. 29, 2018

(86) PCT No.: PCT/JP2018/032025
§ 371 (c)(1),
(2) Date: Mar. 9, 2020

(87) PCT Pub. No.: WO2019/049758
PCT Pub. Date: Mar. 14, 2019

(65) Prior Publication Data
US 2020/0261278 A1 Aug. 20, 2020

(30) Foreign Application Priority Data

Sep. 11, 2017 (JP) .............................. JP2017-173692
Nov. 30, 2017 (JP) .............................. JP2017-230735

(51) Int. Cl.
*A61F 13/42* (2006.01)
*H04B 1/3827* (2015.01)
(Continued)

(52) U.S. Cl.
CPC ........... *A61F 13/42* (2013.01); *G01N 27/048* (2013.01); *H01Q 1/273* (2013.01); *H04B 1/385* (2013.01); *A61F 2013/424* (2013.01)

(58) Field of Classification Search
CPC ...... A61F 13/42; A61F 2013/424; A61F 5/44; G01N 27/048; G01N 27/223; G01N 27/227; H01Q 1/273; H04B 1/385; H01L 51/00
See application file for complete search history.

(56) References Cited

U.S. PATENT DOCUMENTS 6,832,507 B1   12/2004  Van De Berg et al.
7,049,969 B2   5/2006   Tamai
(Continued)

FOREIGN PATENT DOCUMENTS

CN    1213529 A    4/1999
GB    1227613 A    4/1971
(Continued)

OTHER PUBLICATIONS

Extended European Search Report for European Application No. 18853951.4, dated Nov. 9, 2020.
(Continued)

*Primary Examiner* — Christopher P McAndrew
*Assistant Examiner* — Zannatul Ferdous
(74) *Attorney, Agent, or Firm* — Birch, Stewart, Kolasch & Birch, LLP

(57) ABSTRACT

The present invention provides a wireless communication device including: a circuit unit; and an antenna which is connected to the circuit unit and which transmits and receives signals to and from a transceiver in a non-contact manner. The wireless communication device transmits dif-
(Continued)

ferent signals to the transceiver, depending on the presence or absence of contact between at least a part of the circuit unit and moisture.

22 Claims, 6 Drawing Sheets

(51) Int. Cl.
*H01Q 1/27* (2006.01)
*G01N 27/04* (2006.01)

(56) References Cited

U.S. PATENT DOCUMENTS

| | | | |
|---|---|---|---|
| 2004/0036484 A1 | 2/2004 | Tamai | |
| 2013/0036802 A1 | 2/2013 | Johnson et al. | |
| 2014/0148772 A1* | 5/2014 | Hu | A61F 13/15699 604/385.01 |
| 2014/0303470 A1* | 10/2014 | Tsukada | D06M 11/74 428/394 |
| 2014/0358099 A1 | 12/2014 | Durgin et al. | |
| 2016/0050757 A1* | 2/2016 | Diao | H05K 1/162 336/200 |
| 2018/0325743 A1* | 11/2018 | Ho | A61F 13/42 |
| 2018/0331586 A1* | 11/2018 | Hao | H04B 5/0081 |
| 2018/0333306 A1* | 11/2018 | Ahong | A61B 5/6843 |
| 2018/0352367 A1* | 12/2018 | Withers | A46B 15/001 |
| 2019/0293591 A1* | 9/2019 | Iwata | G01N 27/223 |

FOREIGN PATENT DOCUMENTS

| | | |
|---|---|---|
| GB | 2524288 A | 9/2015 |
| JP | 2006-349418 A | 12/2006 |
| JP | 2014-529732 A | 11/2014 |
| JP | 2016-38256 A | 3/2016 |
| JP | 2017-102028 A | 6/2017 |
| JP | 2017-150889 A | 8/2017 |
| TW | 201632158 A | 9/2016 |
| WO | WO 2015/140394 A1 | 9/2015 |

OTHER PUBLICATIONS

Han et al., "Carbon Nanotube Based Humidity Sensor on Cellulose Paper," Journal of Physical Chemistry C, vol. 116, 2012, pp. 22094-22097, 4 pages total.
Lee et al, "Carbon nanotube p-n junction diodes," Applied Physics Letters, vol. 85, No. 1, Jul. 5, 2004, pp. 145-147, 3 pages total.
Otero et al., "Impedance studies of electrogenerated polypyrrole films," Synthetic Metals, vol. 51, 1992, pp. 87-94, 8 pages total.
Singh et al., "Junction properties of aluminum/polypyrrole (polypyrrole derivatives) Schottky diodes," Applied Physics Letters, vol. 71, No. 19, Nov. 10, 1997, pp. 2845-2847, 3 pages total.
Torsi et al., "NTCDA organic thin-film-transistor as humidity sensor: weaknesses and strengths," Sensors and Actuators B, vol. 77, 2001, pp. 7-11, 5 pages total.
Yang et al., "Sol-Gel Zinc Oxide Humidity Sensors Integrated with a Ring Oscillator Circuit On-a-Chip," Sensors, vol. 14, 2014, 20360-20371, 12 pages total.
Zhao et al., "Carbon nanotubes humidity sensor based on high testing frequencies," Sensors and Actuators A, vol. 168, 2011, pp. 10-13, 4 pages total.
Zhu et al., "Humidity sensors based on pentacene thin-film transistors," Applied Physics Letters, vol. 81, No. 24, Dec. 9, 2002, pp. 4643-4645, 3 pages total.
Ziai et al., "Smart radio-frequency identification tag for diaper moisture detection," Healthcare Technology Letters, vol. 2, No. 1, 2015, pp. 18-21, 4 pages total.
Chinese Office Action and Search Report for Chinese Application No. 201880058563.2 dated Jan. 6, 2022.
International Search Report, issued in PCT/JP2018/032025, PCT/ISA/210, dated Oct. 23, 2018.
Nakajima et al., "Development of Urination Detection System using RFID technology", The transactions of the Institute of Electronics, Information and Communication Engineers, B, vol. J96-B, No. 12, Dec. 1, 2013, p. 1378-1385.
Written Opinion of the International Searching Authority, issued in PCT/JP2018/032025, PCT/ISA/237, dated Oct. 23, 2018.
Taiwanese Office Action and Search Report for Taiwanese Application No. 107130853, dated Apr. 6, 2022.
European Office Action for European Application No. 18853951.4, dated May 11, 2022.
Hossein-Babaei Faramarz et al. "A gold/organic semiconductor diode for ppm-level humidity sensing", Sensors and Actuators B: vol. 205, Aug. 24, 2014, pp. 143-150, 8 pages total.

* cited by examiner

WIRELESS COMMUNICATION DEVICE, DIAPER AND MOISTURE DETECTING SYSTEM

TECHNICAL FIELD

The present invention relates to a wireless communication device, as well as a diaper and a moisture detection system including the wireless communication device.

BACKGROUND ART

Conventionally, systems using RFID (Radio Frequency Identification) are known as techniques for detecting the presence of moisture. For medical applications, in particular, a technique is known in which a wireless communication device such as an IC tag is embedded in a diaper, in order to detect moisture generated due to urination and the like of a care receiver.

For example, Non-patent Literature 1 discloses a technique in which a reader transmits a radio signal having a frequency of 950 MHz (UHF band) to an IC tag, and moisture is detected using the reflected signal to the transmitted signal. This technique achieves the detection of moisture utilizing changes in the reflection coefficient which occur when an antenna gets wet.

Further, Patent Literature 1 also discloses a technique in which an IC tag including a wetness detection terminal is provided in a diaper, and the presence or absence of moisture is detected depending on the fluctuation of the voltage value of the wetness detection terminal. In this technique, when the wetness detection terminal detects the presence of wetness, the IC tag transmits a signal different from the signal to be transmitted in a dried state, or does not transmit a signal, and the reader communicating with the IC tag detects the state of wetness of the IC tag, depending on the type of the signal to be received or the presence or absence of a signal.

CITATION LIST

Patent Literature

Patent Literature 1: JP 2006-349418 A

Non-Patent Literature

Non-patent Literature 1: Hiromasa NAKAJIMA and three others "Development of Urination Detection System using RFID technology", The transactions of the Institute of Electronics, Information and Communication Engineers, B, Vol. J96-B, No. 12, pp. 1378 to 1385, Dec. 1, 2013.

SUMMARY OF INVENTION

Technical Problem

However, in the technique disclosed in Non-patent Literature 1, the generation of moisture causes the absorption of radio waves as well as large changes in the impedance of the antenna, and the receiving sensitivity of the IC tag is markedly reduced to result in a failure to communicate with the reader. Therefore, it is impossible to distinguish, on the side of the reader, the generation of moisture from the breakage of the IC chip in the IC tag.

Further, in the technique disclosed in Patent Literature 1, a complex configuration is needed in order to change the state or the function of the IC chip depending on the detection result of the wetness detection terminal.

The present invention has been made in view of the above described problems, and an object of the invention is to provide a wireless communication device which enables to accurately detect the generation of moisture with a simple configuration, as well as a diaper and a moisture detection system including the wireless communication device.

Solution to Problem

In order to solve the above mentioned problems and to achieve the object, the wireless communication device according to the present invention includes: a circuit unit; and an antenna which is connected to the circuit unit and which transmits and receives signals to and from a transceiver in a non-contact manner; wherein the wireless communication device transmits different signals to the transceiver, depending on the presence or absence of contact between at least a part of the circuit unit and moisture.

In the wireless communication device according to the present invention described above, the circuit unit includes an element formed using one or more materials selected from the group consisting of carbon nanotubes, graphene, fullerene and organic semiconductors, and the properties of the element change due to contact with moisture.

In the wireless communication device according to the present invention described above, at least one parameter of the signal returned in response to the signal received from the transceiver changes, when the properties of the element change.

In the wireless communication device according to the present invention described above, the element includes a diode; and when the diode comes into contact with moisture, the wireless communication device transmits to the transceiver, a signal different from the signal to be transmitted when the diode is not in contact with moisture.

In the wireless communication device according to the present invention described above, the diode is a variable capacity diode; and when the variable capacity diode comes into contact with moisture, the wireless communication device transmits to the transceiver, a signal having an intensity different from the intensity of the signal to be transmitted when the variable capacity diode is not in contact with moisture.

In the wireless communication device according to the present invention described above, the circuit unit further includes an oscillator circuit; and when the diode comes into contact with moisture, the wireless communication device transmits to the transceiver, a signal having a frequency different from the frequency of the signal to be transmitted when the diode is not in contact with moisture.

In the wireless communication device according to the present invention described above, the oscillator circuit includes a ring oscillator.

In the wireless communication device according to the present invention described above, the element is a ring oscillator; and when the ring oscillator comes into contact with moisture, the wireless communication device transmits to the transceiver, a signal having a frequency different from the frequency of the signal to be transmitted when the ring oscillator is not in contact with moisture.

In the wireless communication device according to the present invention described above, the element is a memory element; and when the memory element comes into contact with moisture, the wireless communication device transmits to the transceiver, a signal different from the signal to be transmitted when the memory element is not in contact with moisture.

In the wireless communication device according to the present invention described above, the element is formed using a carbon nanotube.

In the wireless communication device according to the present invention described above, a semiconductor layer included in the element is formed using a carbon nanotube.

In the wireless communication device according to the present invention described above, the wireless communication device transmits signals including different information to the transceiver, depending on the presence or absence of contact between at least a part of wiring included in the circuit unit and moisture.

In the wireless communication device according to the present invention described above, the circuit unit includes a digital circuit; and when at least a part of wiring of the digital circuit comes into contact with moisture, the properties of the digital circuit change, and the wireless communication device transmits to the transceiver, a signal including information different from the information included in the signal to be transmitted when at least a part of the wiring is not in contact with moisture.

In the wireless communication device according to the present invention described above, the electrical resistance of the wiring changes, when at least a part of the wiring comes into contact with moisture.

In the wireless communication device according to the present invention described above, at least a part of the wiring contains electrically conductive particles and a water-soluble resin.

In the wireless communication device according to the present invention described above, at least a part of the wiring contains a water-soluble electrically conductive polymer.

In the wireless communication device according to the present invention described above, at least a part the wiring contains electrically conductive particles and a water-absorbent resin.

In the wireless communication device according to the present invention described above, at least a part of the wiring is provided on a layer containing a water-soluble resin; and the electrical resistance of the wiring changes, when the layer comes into contact with moisture.

In the wireless communication device according to the present invention described above, at least a part of the wiring is provided on a layer containing a water-absorbent resin; and the electrical resistance of the wiring changes, when the layer comes into contact with moisture.

In the wireless communication device according to the present invention described above,
the circuit unit includes:
a memory element which is connected to the wiring and which stores predetermined information; and
a control circuit which reads information from the memory element and transmits the information to the transceiver; and
the information to be read by the control circuit from the memory element varies depending on the presence or absence of contact between the wiring and moisture.

In the wireless communication device according to the present invention described above,
the circuit unit includes:
a plurality of memory elements arranged in the form of an array; and
a control circuit which reads information from the plurality of memory elements and transmits the information to the transceiver; and
the information to be read by the control circuit from the plurality of memory elements varies depending on the presence or absence of contact between the wiring and moisture.

The diaper according to the present invention includes:
a water absorbent material which absorbs and retains moisture; and
a waterproof material having a waterproof function and covering the water absorbent material;
wherein the diaper is capable of being attached to a human body and absorbing moisture released from the human body; and
wherein the diaper includes the wireless communication device according to the above described invention.

In the diaper according to the present invention described above, the wireless communication device is positioned between the water absorbent material and the waterproof material.

The moisture detection system according to the present invention includes:
the wireless communication device according to the above described invention; and
a transceiver which is capable of communicating with the wireless communication device in a non-contact manner, and which detects the presence or absence of contact between the wireless communication device with moisture, based on the signal returned in response to the signal transmitted to the wireless communication device.

In the moisture detection system according to the present invention described above, the transceiver transmits a signal having a frequency in the UHF band or the microwave band.

In the moisture detection system according to the present invention described above,
the wireless communication device is provided in a diaper including:
a water absorbent material which absorbs and retains moisture; and
a waterproof material having a waterproof function and covering the water absorbent material; and
wherein the diaper is capable of being attached to a human body and absorbing moisture released from the human body.

Advantageous Effects of Invention

According to the present invention, it is possible to accurately detect the generation of moisture with a simple configuration.

DESCRIPTION OF EMBODIMENTS

The embodiments for carrying out the present invention (hereinafter, each referred to as "embodiment") will be described with reference to accompanying drawings.

Embodiment 1

Figure 1:
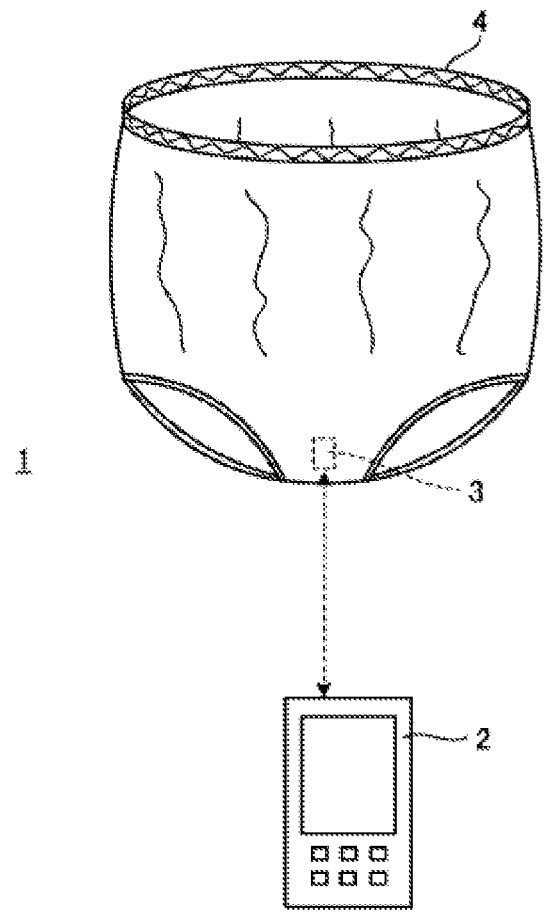
FIG. 1 is a diagram showing the configuration of the moisture detection system according to Embodiment 1 of the present invention.

FIG. 1 is a diagram showing the configuration of the moisture detection system according to Embodiment 1 of the present invention. A moisture detection system 1 shown in FIG. 1 includes: a transceiver 2 which wirelessly transmits and receives signals in a predetermined frequency band; and a diaper 4 which includes a wireless communication device 3 capable of non-contact communication (wireless communication) with the transceiver 2, and which is capable of being attached to a human body and absorbing moisture at the time of urination. The moisture detection system 1 is a system for detecting the generation of moisture due to urination and the like of a person wearing the diaper 4, and therefore, it can be said that the moisture detection system 1 is a wetness detection system using the diaper 4.

The transceiver 2 includes: an antenna which transmits and receives signals in a predetermined frequency band, a CPU (Central Processing Unit) for controlling operations, and a memory for storing various types of information. The transceiver 2 transmits a signal (carrier wave) in a predetermined frequency band to the wireless communication device 3, and receives a return signal in response to the transmitted signal. The return signal includes information specific to the wireless communication device 3. The transceiver 2 distinguishes the wireless communication device 3 based on the signal received from the wireless communication device 3, and at the same time, detects whether the wireless communication device 3 is in a state in contact with moisture or not. The signal to be transmitted by the transceiver 2 is, for example, a radio wave having a frequency in the UHF band (860 to 960 MHz) or the microwave band (2.45 GHz). The transceiver 2 as described above may be configured, for example, as a dedicated terminal such as a reader/writer, or may be configured using a mobile terminal such as a smart phone.

Figure 2:
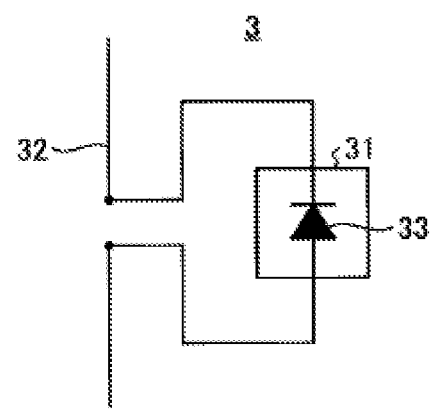
FIG. 2 is a diagram showing the circuit configuration of the wireless communication device according to Embodiment 1 of the present invention.

FIG. 2 is a diagram showing the circuit configuration of the wireless communication device 3. The wireless communication device 3 includes a circuit unit 31, and an antenna 32 connected to the circuit unit 31. The wireless communication device 3 receives a signal (carrier wave) transmitted by the transceiver 2, and using this signal as an energy source, returns a signal (reflection wave) to which information specific to the wireless communication device 3 is added.

The circuit unit 31 includes a diode 33. The diode 33 is an element formed using one or more materials selected from the group consisting of carbon nanotubes, graphene, fullerene and organic semiconductors.

Examples of the organic semiconductor to be used for forming the diode 33 include polythiophenes, polypyrroles, poly(p-phenylene vinylene)s such as poly(p-phenylene vinylene), polyanilines, polyacetylenes, polydiacetylenes, polycarbazoles, polyfurans, polyheteroaryls, condensed polycyclic low-molecular-weight compound semiconductors, low-molecular-weight compound semiconductors containing a heteroaromatic ring. Examples of the polythiophenes include poly-3-hexylthiophene and polybenzothiophene. Examples of the polyfurans include polyfuran and polybenzofuran. Examples of the polyheteroaryls include those containing a nitrogen-containing aromatic ring as a structural unit, such as pyridine, quinoline, phenanthroline, oxazole and oxadiazole. Examples of the condensed polycyclic low-molecular-weight compound semiconductors include anthracene, pyrene, naphthacene, pentacene, hexacene and rubrene. Examples of the low-molecular-weight compound semiconductors containing a heteroaromatic ring include furan, thiophene, benzothiophene, dibenzofuran, pyridine, quinoline, phenanthroline, oxazole and oxadiazole. These materials enable the formation of the diode on a film by a coating method, and therefore, the use of such materials allows for an easier production as compared to commonly used materials, such as silicon. At the same time, it is possible to achieve a reduction in cost, making the production economically efficient.

Further, the diode 33 more preferably contains a carbon nanotube, from the viewpoint of enabling the formation of the diode at a low temperature of 200° C. or lower, having high semiconductor properties, and the like. Among carbon nanotubes, particularly preferred is a carbon nanotube composite having a conjugated polymer attached to at least a part of the surface thereof. This is because the use of such a carbon nanotube composite enables to uniformly dissolve the carbon nanotube in a solution, without compromising high electrical properties of the carbon nanotube. By using a solution in which a carbon nanotube is uniformly dispersed, it is possible to form a film in which the carbon nanotube is uniformly dispersed, by a coating method such as an ink jet method.

The diode 33 includes, for example, a pair of electrodes provided on the surface of an insulating substrate, and a semiconductor layer formed between the pair of electrodes. The semiconductor layer contains, for example, a carbon nanotube. The configuration of the diode 33 is not particularly limited, and other configurations are disclosed, for example, in WO 2016/158862.

The antenna 32 is connected to the circuit unit 31, and transmits and receives signals to and from the transceiver 2. The antenna 32 is a dipole antenna, and the impedance of the antenna is matched with the diode 33. The antenna 32 may also be a loop antenna or the like.

Figure 3:
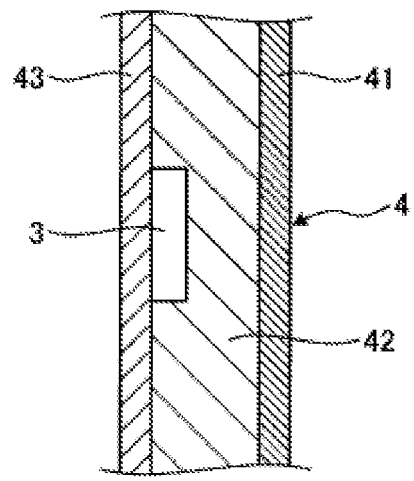
FIG. 3 is a partial sectional view showing the configuration of the main portion of the diaper.

FIG. 3 is a schematic partial sectional view showing the configuration of the main portion of the diaper 4. The diaper 4 is formed using a nonwoven fabric or the like, and includes: a surface material 41 which comes into direct contact with human skin; a water absorbent material 42 which is formed using a super absorbent polymer or the like, and which absorbs and retains moisture that has passed through the surface material 41; and a waterproof material 43 which is composed of a sheet-like material having waterproof properties, and which constitute an exterior body located on the outer surface side of the diaper 4, of the surfaces of the water absorbent material 42. The wireless communication device 3 is provided between the water absorbent material 42 and the waterproof material 43. The wireless communication device 3 is preferably provided at a position at which the water absorbent material 42 more easily absorbs moisture at the time of urination, in other words, a position within the region which, when a person wears the diaper 4 and urinates, is more likely to get wet by the urine.

When a person wearing the diaper 4 having the above described configuration releases moisture out of the body, by urination and the like, the water absorbent material 42 absorbs the moisture. When the moisture absorbed by the water absorbent material 42 reaches the diode 33, the diode 33 comes into contact with the moisture to be in a wet state, thereby causing changes in the rectification properties of the diode 33. The changes in the rectification properties of the diode 33 cause changes in signal intensity, which is one of the parameters of the signal to be returned from the wireless communication device 3 to the transceiver 2, as compared to the case in which the diode 33 is in a dry state. The transceiver 2 detects whether the diode 33 is in contact with moisture or not, that is, whether the diaper 4 is in a wet state or not, based on the intensity of the signal received from the wireless communication device 3.

According to Embodiment 1 of the present invention described above, it is possible to accurately detect the generation of moisture with a simple configuration. This is because the circuit unit 31 is formed using the diode 33, which is formed using one or more materials selected from the group consisting of carbon nanotubes, graphene, fullerene and organic semiconductors, and when the diode 33 comes into contact with moisture, the semiconductor properties of the diode or the electrostatic capacity of the insulating layer of the diode change(s), and as a result, the wireless communication device 3 outputs a signal having an intensity different from the intensity of the signal to be output when the diode 33 is not in contact with moisture.

Further, according to Embodiment 1 of the present invention, materials capable of forming a film are used in the circuit unit 31, and this allows for an easier production as compared to using materials commonly used for semiconductors, such as silicon. At the same time, it is possible to achieve a reduction in cost, making the production economically efficient. In this regard, the wireless communication device 3 according to Embodiment 1 of the present invention is suitable for mass-produced products such as the diaper 4.

Embodiment 2

Figure 4:
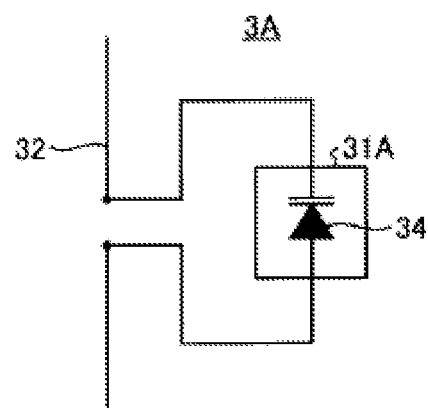
FIG. 4 is a diagram showing the configuration of the wireless communication device according to Embodiment 2 of the present invention.

FIG. 4 is a diagram showing the configuration of the wireless communication device included in the moisture detection system according to Embodiment 2 of the present invention. A wireless communication device 3A shown in FIG. 4 is provided in the diaper 4, in the same manner as in Embodiment 1, and includes a circuit unit 31A and the antenna 32. The circuit unit 31A includes a variable capacity diode 34 whose electrostatic capacity changes corresponding to the voltage applied. The configuration of the moisture detection system, excluding the circuit unit 31A, is the same as that of Embodiment 1.

The variable capacity diode 34 is an element formed using one or more materials selected from the group consisting of carbon nanotubes, graphene, fullerene and organic semiconductors. In the variable capacity diode 34 formed using the above described material(s), the properties of the diode change due to contact with moisture. The properties of the variable capacity diode 34 as used herein refer to the semiconductor properties of the diode or the electrostatic capacity of the insulating layer of the diode. As a result of changes in the properties of the variable capacity diode 34, the intensity, which is one of the parameters of the signal to be returned to the transceiver 2, changes from the intensity of the signal to be returned when the diode is in a dry state.

According to Embodiment 2 of the present invention described above, it is possible to accurately detect the generation of moisture with a simple configuration, in the same manner as in Embodiment 1. Further, Embodiment 2 of the present invention allows for an easier and economically efficient production, in the same manner as Embodiment 1.

Embodiment 3

Figure 5:
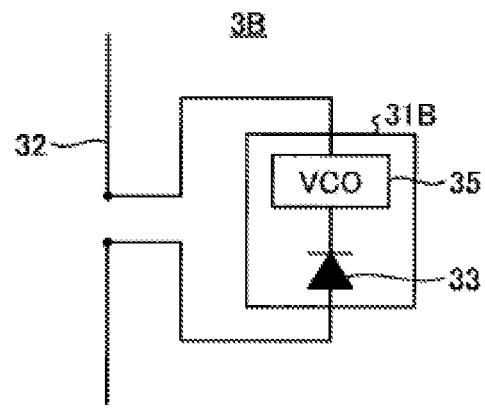
FIG. 5 is a diagram showing the configuration of the wireless communication device according to Embodiment 3 of the present invention.

FIG. 5 is a diagram showing the configuration of the wireless communication device included in the moisture detection system according to Embodiment 3 of the present invention. A wireless communication device 3B shown in FIG. 5 is provided in the diaper 4, in the same manner as in Embodiment 1, and includes a circuit unit 31B and the antenna 32. The circuit unit 31B includes the diode 33 and a voltage controlled oscillator (VCO) 35. The configuration of the moisture detection system, excluding the circuit unit 31B, is the same as that of Embodiment 1.

The voltage controlled oscillator 35 is an oscillator which controls the oscillatory frequency by the voltage to be input. The voltage controlled oscillator 35 is, for example, an oscillator circuit formed using a coil or a capacitor. The circuit unit 31B may further include a switching element such as a transistor. In this case, the switching element is turned on and off, corresponding to the signal whose oscillatory frequency is controlled by the voltage controlled oscillator 35. It is decided whether the wireless communication device 3B returns a signal to the transceiver 2 or not, corresponding to the turning on and off of the switching element. Further, the voltage controlled oscillator 35 may be formed using a ring oscillator. The use of a ring oscillator enables to form an oscillator circuit which is simpler than one formed using a coil or a capacitor. The ring oscillator is formed using a material such as silicon, and changes in the properties due to contact with moisture do not occur in the ring oscillator.

In the wireless communication device 3B having the above described configuration, when the diode 33 comes into contact with moisture to be in a wet state, and thus causes changes in the rectification properties of the diode, the oscillatory properties of the voltage controlled oscillator 35 change. As a result, the frequency, which is one of the parameters of the signal passing through the circuit unit 31B, changes. Therefore, the frequency of the signal returned to the transceiver 2 from the wireless communication device 3B when the diode 33 is in a wet state, is different from the frequency of the signal returned from the wireless communication device 3B when the diode 33 is not in contact with moisture and is in a dry state. The transceiver 2 detects the presence or absence of moisture, based on the frequency of the signal received from the wireless communication device 3B.

According to Embodiment 3 of the present invention described above, it is possible to accurately detect the generation of moisture with a simple configuration, in the same manner as in Embodiment 1. Further, Embodiment 3 of the present invention allows for an easier and economically efficient production, in the same manner as Embodiment 1.

In addition, according to Embodiment 3 of the present invention, moisture is detected based on changes in the frequency of the signal received by the transceiver 2. Therefore, the degree of freedom in the positional relationship between the transceiver 2 and the wireless communication device 3B, for carrying out a proper communication, is higher as compared to that in Embodiment 1 in which changes in the intensity, which is a parameter sensitive to changes in the distance, is detected.

Modified Example 1 of Embodiment 3

Figure 6:
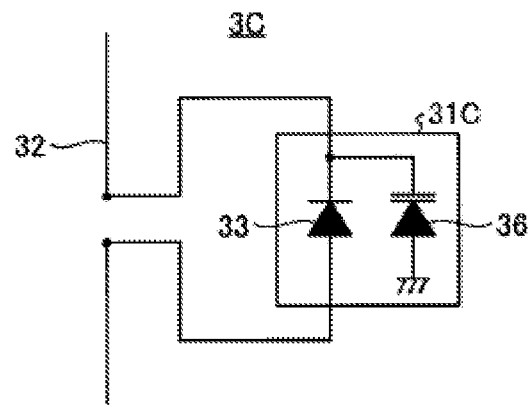
FIG. 6 is a diagram showing the configuration of the wireless communication device according to Modified Example 1 of Embodiment 3 of the present invention.

FIG. 6 is a diagram showing the configuration of the wireless communication device according to Modified Example 1 of Embodiment 3 of the present invention. A wireless communication device 3C shown in FIG. 6 includes a circuit unit 31C and the antenna 32. The circuit unit 31C includes the diode 33, and a variable capacity diode 36 whose cathode side is connected in parallel to the diode 33 and whose anode side is connected to the ground.

The variable capacity diode 36 has the function of a voltage controlled oscillator. The variable capacity diode 36 is an element formed using one or more materials selected from the group consisting of carbon nanotubes, graphene, fullerene and organic semiconductors, and the semiconductor properties of the variable capacity diode 36 or the electrostatic capacity of the insulating layer of the diode change(s) due to contact with moisture.

In the wireless communication device 3C having the above described configuration, the frequency of the signal returned to the transceiver 2 from the wireless communication device 3C when the diode 33 is in a wet state, is different from the frequency of the signal returned to the transceiver 2 when the diode 33 is in a dry state. Further, the intensity of the signal returned to the transceiver 2 when the variable capacity diode 36 is in a wet state, is different from the intensity of the signal returned to the transceiver 2 when the variable capacity diode 36 is in a dry state. The transceiver 2 detects the presence or absence of moisture, based on the frequency and/or the intensity of the signal received from the wireless communication device 3C.

According to Modified Example 1 of Embodiment 3 described above, it is possible to obtain the same effect as that obtained in Embodiment 3.

Modified Example 2 of Embodiment 3

Figure 7:
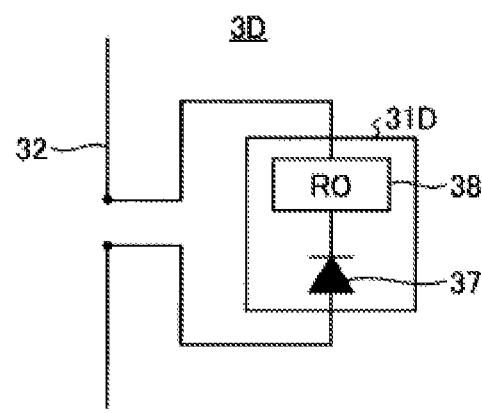
FIG. 7 is a diagram showing the configuration of the wireless communication device according to Modified Example 2 of Embodiment 3 of the present invention.

FIG. 7 is a diagram showing the configuration of the wireless communication device according to Modified Example 2 of Embodiment 3 of the present invention. A wireless communication device 3D shown in FIG. 7 includes a circuit unit 31D and the antenna 32. The circuit unit 31D includes a diode 37, and a ring oscillator (RO) 38 connected in series to the diode 37. In the present Modified Example 2, the diode 37 is formed using a material such as silicon, and changes in the properties of the diode due to contact with moisture do not occur in the diode 37.

The ring oscillator 38 has the function of a voltage controlled oscillator. The ring oscillator 38 includes a transistor formed using one or more materials selected from the group consisting of carbon nanotubes, graphene, fullerene and organic semiconductors. In the ring oscillator 38 formed using such a transistor, the oscillatory properties change due to contact with moisture. The changes in the oscillatory properties of the ring oscillator 38 cause changes in the frequency of the signal passing through the circuit unit 31D. Further, the circuit unit 31D may further include a switching element such as a transistor. The switching element is turned on and off, corresponding to the signal whose oscillatory frequency is controlled by the ring oscillator 38. It is decided whether the wireless communication device 3D returns a signal to the transceiver 2 or not, corresponding to the turning on and off of the switching element. Depending on the configuration of the ring oscillator 38, there are cases where changes in the oscillatory properties cause changes in the intensity of the signal passing through the circuit unit 31D. The ring oscillator 38 is formed, for example, by combining a plurality of thin film transistors. The semiconductor layer in each thin film transistor contains, for example, a carbon nanotube.

In the wireless communication device 3D having the above described configuration, the frequency of the signal returned to the transceiver 2 from the wireless communication device 3D when the ring oscillator 38 is in a wet state, is different from the frequency of the signal returned to the transceiver 2 when the ring oscillator 38 is in a dry state. The transceiver 2 detects the presence or absence of moisture based on the frequency of the signal received from the wireless communication device 3D.

According to Modified Example 2 of Embodiment 3 described above, it is possible to obtain the same effect as that obtained in Embodiment 3.

In the present Modified Example 2, the diode 33 used in Embodiment 1 may be used instead of the diode 37. In this case, the transceiver 2 may detect the presence or absence of moisture, by further using the intensity of the signal returned from the wireless communication device.

Further, in the present Modified Example 2, the diode 33 used in Embodiment 1 may be used instead of the diode 37, and a protective layer may be provided to the diode 33 so as to protect the diode 33 from the effect of moisture. In this case, the transceiver 2 detects the presence or absence of moisture based on the frequency of the signal received from the wireless communication device.

The protective layer is required to cover at least the semiconductor layer in the diode 37, and may cover the entirety of the diode 37. Further, the protective layer may cover the entirety of the transceiver 2 excluding the ring oscillator 38.

The material to be used for forming the protective layer is not particularly limited, and examples thereof include the following materials:
inorganic materials such as silicon oxide and alumina;
organic polymer materials such as polyimides and derivatives thereof, polyvinyl alcohol, polyvinyl chloride, polyethylene terephthalate, polyvinylidene fluoride, polysiloxanes and derivatives thereof, and polyvinyl phenol and derivatives thereof; and
mixtures of powders of inorganic materials and organic polymer materials, and mixtures of organic low-molecular-weight materials and organic polymer materials.

Among these, it is preferred to use an organic polymer material which allows for forming the protective layer by a coating method.

Embodiment 4

Figure 8:
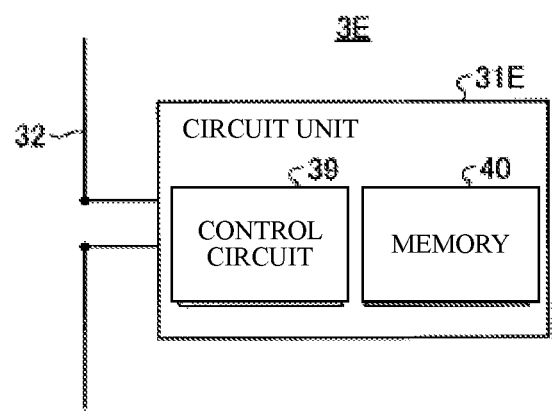
FIG. 8 is a diagram showing the configuration of the wireless communication device according to Embodiment 4 of the present invention.

FIG. 8 is a diagram showing a configuration example of the wireless communication device included in the moisture detection system according to Embodiment 4 of the present invention. A wireless communication device 3E shown in FIG. 8 is provided in the diaper 4, in the same manner as in Embodiment 1, and includes a circuit unit 31E and the antenna 32. The circuit unit 31E is a digital circuit including a control circuit 39 and a memory 40. The control circuit 39 includes a CMOS (complementary metal oxide semiconductor) circuit or a rectifier circuit. When the control circuit 39 receives a signal from the transceiver 2, the control circuit 39 reads the information stored in the memory 40 and returns a signal to the transceiver 2. The configuration of the moisture detection system, excluding the circuit unit 31E, is the same as that of Embodiment 1.

Figure 9:
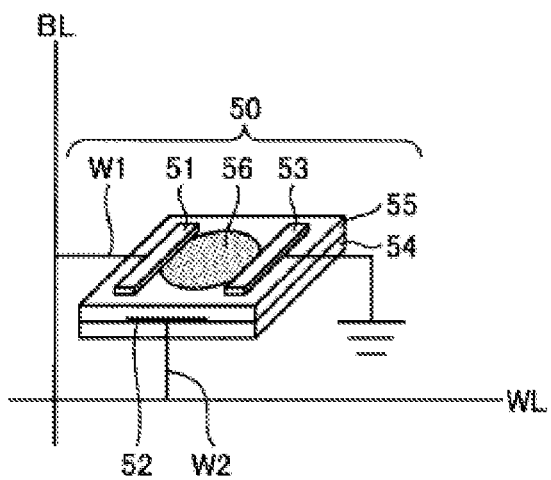
FIG. 9 is a schematic diagram showing the configuration of the main portion of the memory included in the wireless communication device according to Embodiment 4 of the present invention.

FIG. 9 is a schematic diagram showing the configuration of the main portion of the memory 40. The memory 40 includes one memory element 50. The memory element 50 is a thin film transistor (TFT) including a source 51, a gate 52 and a drain 53. The source 51 is connected to a bit line BL through a wiring W1, the gate 52 is connected to a word line WL through a wiring W2, and the drain 53 is connected to the ground.

Figure 10:
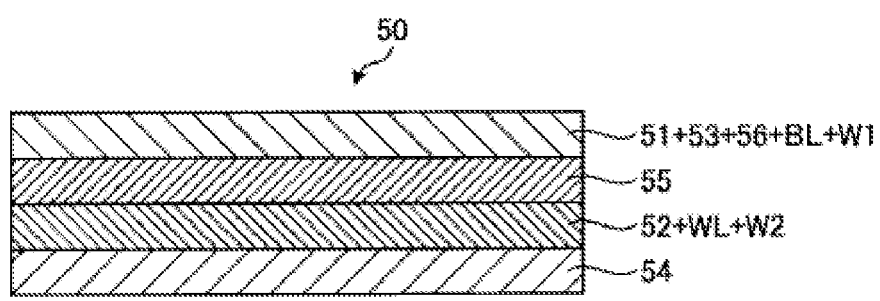
FIG. 10 is a schematic diagram showing the laminated structure of the memory element.

FIG. 10 is a schematic diagram showing the laminated structure of the memory element 50. The FIG. 10 is a diagram for showing the positional relationship between the respective layers, and the thickness of each layer is irrelevant. The memory element 50 includes: a substrate 54; the gate 52, the wiring W2 and the word line WL which are collectively formed on the substrate 54; and an insulating layer 55 laminated on top thereof. On top of the insulating layer 55, a semiconductor layer 56 is formed. The semiconductor layer 56 is collectively formed with the source 51, the drain 53, the wiring W1 and the bit line BL. As described above, the memory element 50 has a so-called bottom-gate configuration. The memory element 50 can also be formed to have a top-gate configuration.

The substrate 54 may be made of any material, as long as at least the surface of the substrate on which the electrode system is provided has insulation properties. Examples of the material which can be suitably used include: inorganic materials such as silicon wafers, glass, sapphire and alumina sintered bodies; and organic materials such as polyimides, polyvinyl alcohol, polyvinyl chloride, polyethylene terephthalate, polyvinylidene fluoride, polysiloxanes, polyvinyl phenol (PVP), polyesters, polycarbonates, polysulfone, polyethersulfone, polyethylene, polyphenylene sulfide and polyparaxylene. Further, the substrate 54 may be, for example, a substrate obtained by laminating a plurality of materials, such as one obtained by forming a PVP film on a silicon wafer, or one obtained by forming a polysiloxane film on a polyethylene terephthalate.

The material to be used for forming the insulating layer 55 is not particularly limited, as long as the material has insulation properties sufficient for the resulting insulating layer 55 to function properly. Examples of the material which can be used include polysiloxanes, polyamides, polyamideimides, polyimides, polybenzimidazole, polyvinyl alcohol, polyvinyl phenol, polyacetal, polycarbonates, polyarylates, polyphenylene sulfide, polyethersulfone, polyether ketone, polyphthalamide, polyether nitrile, polymethyl methacrylate, polymethacrylamide, polyvinylidene fluoride, polytetrafluoroethylene, polystyrene, polyesters, aromatic polyethers, novolac resins, phenol resins, acrylic resins, olefin resins, alicyclic olefin resins, vinyl chloride resins, epoxy resins, melamine resins and urea resins. Further, it is also possible to use a material obtained by copolymerizing or mixing any of these polymers with another polymer(s). Among these, a polysiloxane is preferably used, from the viewpoint of improving the on-current of the transistor, and reducing the leak current thereof.

The insulating layer 55 is composed of a single layer or a plurality of layers. In cases where the insulating layer 55 is composed of a plurality of layers, the insulating layer 55 may be formed by laminating a plurality of the insulating layers 55, or by laminating the insulating layer 55 with a known gate insulating layer(s). Further, it is also possible to provide an orientation layer between the insulating layer 55 and the semiconductor layer 56. A known material(s) such as a silane compound, a titanium compound, an organic acid, a hetero-organic acid and/or the like can be used for forming the orientation layer, and an organic silane compound is particularly preferred.

The semiconductor layer 56 is formed using one or more materials selected from the group consisting of carbon nanotubes, graphene, fullerene and organic semiconductors.

Examples of the organic semiconductor to be used for forming the semiconductor layer 56 include polythiophenes, polypyrroles, poly(p-phenylene vinylene)s such as poly(p-phenylene vinylene), polyanilines, polyacetylenes, polydiacetylenes, polycarbazoles, polyfurans, polyheteroaryls, condensed polycyclic low-molecular-weight compound semiconductors, low-molecular-weight compound semiconductors containing a heteroaromatic ring. Examples of the polythiophenes include poly-3-hexylthiophene and polybenzothiophene. Examples of the polyfurans include polyfuran and polybenzofuran. Examples of the polyheteroaryls include those containing a nitrogen-containing aromatic ring as a structural unit, such as pyridine, quinoline, phenanthroline, oxazole and oxadiazole. Examples of the condensed polycyclic low-molecular-weight compound semiconductors include anthracene, pyrene, naphthacene, pentacene, hexacene and rubrene. Examples of the low-molecular-weight compound semiconductors containing a heteroaromatic ring include furan, thiophene, benzothiophene, dibenzofuran, pyridine, quinoline, phenanthroline, oxazole and oxadiazole. These materials enable the formation of the semiconductor layer on a film by a coating method, and therefore, the use of such materials allows for an easier production as compared to commonly used materials, such as silicon. At the same time, it is possible to achieve a reduction in cost, making the production economically efficient.

Further, semiconductor layer 56 more preferably contains a carbon nanotube, from the viewpoint of enabling the formation of the semiconductor layer at a low temperature of 200° C. or lower, having high semiconductor properties, and the like. Among carbon nanotubes, particularly preferred is a carbon nanotube composite having a conjugated polymer attached to at least a part of the surface thereof. This is because the use of such a carbon nanotube composite enables to uniformly dissolve the carbon nanotube in a solution, without impairing high electrical properties of the carbon nanotube. By using a solution in which a carbon nanotube is uniformly dispersed, it is possible to form a film in which the carbon nanotube is uniformly dispersed, by a coating method such as an ink jet method.

In the wireless communication device 3E having the above described configuration, when the memory 40 comes into contact with moisture to be in a wet state, it causes changes in the properties of the semiconductor layer in the memory element 50 included in the memory 40. As a result, the circuit properties of the circuit unit 31E, specifically, the electrical resistance thereof changes, to result in changes in the information (signal value) to be read by the control circuit 39 from the memory 40. For example, in cases where "1" is stored as 1-bit information indicating the normal state, which is a state where the memory 40 is not in contact with moisture, and when the semiconductor layer 56 comes into contact with moisture, the 1-bit information to be read by the control circuit 39 from memory 40 and transmitted to the transceiver 2 changes from "1" to "0". In cases where the 1-bit information included in the signal received from the wireless communication device 3E is different from that in the normal state, the transceiver 2 detects that moisture has attached to the wireless communication device 3E.

According to Embodiment 4 of the present invention described above, it is possible to accurately detect the generation of moisture with a simple configuration, in the same manner as in Embodiment 1. Further, Embodiment 4 of the present invention allows for an easier and economically efficient production, in the same manner as Embodiment 1.

In addition, according to Embodiment 4 of the present invention, moisture is detected based on changes in the information received by the transceiver 2 and stored in the memory 40. Therefore, the degree of freedom in the positional relationship between the transceiver 2 and the wireless communication device 3E, for carrying out a proper communication, is higher as compared to that in Embodiment 1 in which changes in the intensity, which is a parameter sensitive to changes in the distance, is detected.

Modified Example of Embodiment 4

Figure 11:
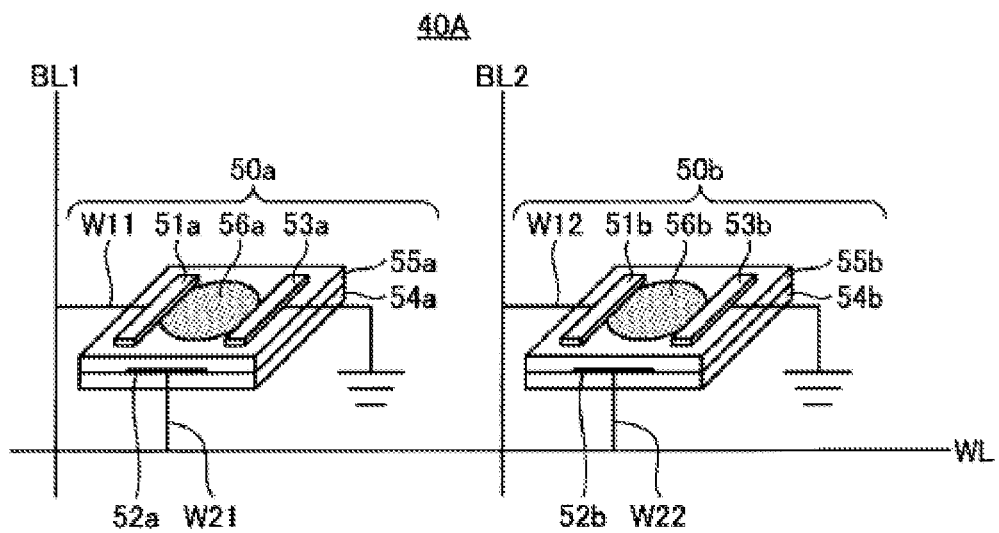
FIG. 11 is a diagram showing the configuration of the main portion of the memory included in the wireless communication device according to Modified Example of Embodiment 4 of the present invention.

FIG. 11 is a diagram showing the configuration of the main portion of the memory included in the wireless communication device according to Modified Example of Embodiment 4. In a memory 40A shown in FIG. 11, two memory elements 50a and 50b are arranged in the form of an array. A source 51a of the memory element 50a is connected to a bit line BL1 through a wiring W11, a source 51b of the memory element 50b is connected to a bit line BL2 through a wiring W12. A gate 52a of the memory element 50a and a gate 52b of the memory element 50b are connected to a common word line WL through a wiring W21 and a wiring W22, respectively. A drain 53a of the memory element 50a and a drain 53b of the memory element 50b are each connected to the ground.

A substrate 54a, an insulating layer 55a and a semiconductor layer 56a of the memory element 50a may be formed in common with, or may be formed individually from, a substrate 54b, an insulating layer 55b and a semiconductor layer 56b of the memory element 50b, respectively. It is more preferred that these two memory elements 50a and 50b be formed as one integrated structure, because it allows for an easier production and enables to contribute to a reduction in size.

In the present Modified Example, the control circuit 39 reads 2-bit information from the memory 40A and transmits to the transceiver 2. For example, in cases where 2-bit information indicating the normal state is "11", and when the control circuit 39 reads another 2-bit information "10", "01" or "00" from the memory 40A and transmits to the transceiver 2, the transceiver 2 detects that the wireless communication device according to the present Modified Example has come into contact with moisture.

According to Modified Example of Embodiment 4 described above, it is possible to obtain the same effect as that obtained in Embodiment 4. The number of memory elements constituting the memory may be 3 or more. In this case, as well, a plurality of memory elements can be arranged in the form of an array, using a common word line.

Embodiment 5

Figure 12:
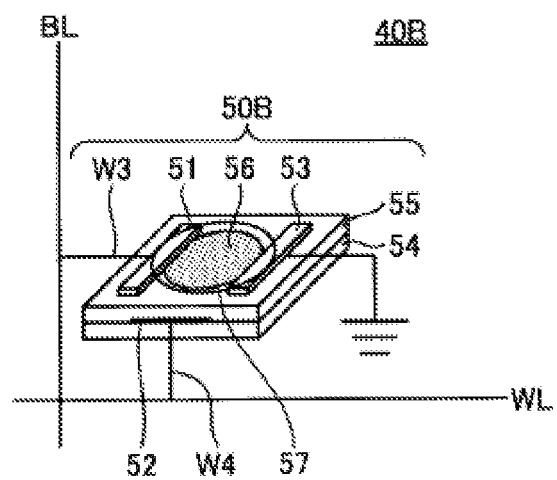
FIG. 12 is a schematic diagram showing the configuration of the main portion of the memory included in the wireless communication device according to Embodiment 5 of the present invention.

FIG. 12 is a schematic diagram showing the configuration of the main portion of the memory included in the wireless communication device according to Embodiment 5 of the present invention. A configuration example of the wireless communication device included in the moisture detection system according to Embodiment 5 of the present invention may be the same as the configuration example of the wireless communication device included in the moisture detection system according to Embodiment 4 shown in FIG. 8. A memory 40B shown in FIG. 12 includes a memory element 50B having a bottom-gate configuration. The memory element 50B includes the source 51, the gate 52, the drain 53, the substrate 54, the insulating layer 55, the semiconductor layer 56 and a second insulating layer 57. The source 51 is connected to the bit line BL through a wiring W3. The gate 52 is connected to the word line WL through a wiring W4. In the memory element 50B, the gate 52, the wiring W4 and the word line WL are collectively formed on the substrate 54, and the insulating layer 55 is laminated on top thereof. On top of the insulating layer 55, the semiconductor layer 56 is formed. The semiconductor layer 56 is collectively formed with the source 51, the drain 53, the wiring W3 and the bit line BL. The second insulating layer 57 is formed on the opposite side of the insulating layer 55, relative to the semiconductor layer 56. The expression "the opposite side of the insulating layer 55, relative to the semiconductor layer 56" refers to the upper side of the semiconductor layer 56, in cases where the insulating layer 55 is formed at the lower side of the semiconductor layer 56, as shown in FIG. 12. The memory element 50B can also be formed to have a top-gate configuration.

Examples of semiconductor materials for forming the semiconductor layer 56 include the same as those described in Embodiment 4, that is, organic semiconductors such as pentacene and polythiophene derivatives; and carbon semiconductors such as carbon nanotubes, graphene and fullerene.

The material to be used for forming the second insulating layer 57 is not particularly limited, and examples thereof include the following materials:
inorganic materials such as silicon oxide and alumina;
organic polymer materials such as polyimides and derivatives thereof, polyvinyl alcohol, polyvinyl chloride, polyethylene terephthalate, polyvinylidene fluoride, polysiloxanes and derivatives thereof, and polyvinyl phenol and derivatives thereof; and
mixtures of powders of inorganic materials and organic polymer materials, and mixtures of organic low-molecular-weight materials and organic polymer materials. Among these, it is preferred to use an organic polymer material which allows for forming the second insulating layer 57 by a coating method.

Since the memory element 50B includes the second insulating layer 57, moisture from the external environment is prevented from coming into contact with the semiconductor material, thereby preventing the occurrence of changes in the properties of the semiconductor material due to contact with moisture. Instead of forming the second insulating layer 57, it is also possible to form the semiconductor layer using a material, such as silicon, whose properties do not change due to contact with moisture, by nature.

The wirings W3 and W4 contain a water-soluble electrically conductive polymer. The water-soluble electrically conductive polymer to be contained in the wirings W3 and W4 is preferably an externally-doped polymer, rather than a self-doped polymer. Specifically, the water-soluble electrically conductive polymer may be, for example, at least one π-conjugated polymer selected from the group consisting of polyparaphenylene, polyphenylene vinylene, polyacetylene, polythiophene, polypyrrole, polyaniline, polyisothianaphthene, polyfuran, polycarbazole, polydiaminoanthraquinone and polyindole, which are unsubstituted or substituted, wherein the skeleton of then-conjugated polymer contains a sulfonic acid group and/or a carboxyl group, or an alkali metal salt, an ammonium salt or a substituted ammonium salt thereof; or contains an alkyl group or an alkyl group containing an ether bond, which is substituted with a sulfonic acid group and/or a carboxy group, or an alkali metal salt, an ammonium salt or a substituted ammonium salt thereof. The water-soluble electrically conductive polymer may also be, for example, a π-conjugated polymer having, on the nitrogen atom, an alkyl group or an alkyl group containing an ether bond, which is substituted with a sulfonic acid group and/or a carboxy group, or an alkali metal salt, an ammonium salt or a substituted ammonium salt thereof, or substituted with a sulfonic acid group and/or a carboxyl group, or an alkali metal salt, an ammonium salt or a substituted ammonium salt thereof.

In the case of the memory element 50B shown in FIG. 12, which has a bottom-gate configuration, it is preferred that at least the wiring W3, which is more susceptible to coming into contact with moisture as compared to the wiring W4, be formed using any of the materials described above. In this case, the wiring W4 may be formed using an electrically conductive material. In cases where the memory element has a top-gate configuration, the wiring W4 connected to the gate 52 is more susceptible to coming into contact with moisture as compared to the wiring W3 connected to the source 51. Therefore, it is preferred that at least the wiring W4 be formed using any of the materials described above. In this case, the wiring W3 may be formed using an electrically conductive material.

In the wireless communication device according to Embodiment 5 of the present invention, when the memory 40B comes into contact with moisture to be in a wet state, and the wiring W3 and/or W4 come(s) into contact with moisture, the water-soluble electrically conductive polymer is dissolved to cause disconnection of the wiring(s), leading to an increase in resistance. This results in changes in the information to be read by the control circuit 39 from the memory 40B, in the same manner as in Embodiment 4. In cases where the 1-bit information included in the signal received from the wireless communication device according to Embodiment 5 of the present invention is different from that in the normal state, the transceiver 2 detects that moisture has attached to the wireless communication device according to Embodiment 5 of the present invention.

In Embodiment 5 of the present invention, it is possible to obtain the same effect as that obtained in Modified Example of Embodiment 4, by providing two memory elements in the form of an array, in the same manner as in Modified Example of Embodiment 4 shown in FIG. 11. The number of memory elements constituting the memory may be 3 or more. In this case, as well, a plurality of memory elements can be arranged in the form of an array, using a common word line.

According to Embodiment 5 of the present invention described above, it is possible to accurately detect the generation of moisture with a simple configuration, since the wireless communication device transmits to the transceiver 2, a signal including different information, depending on the presence or absence of contact between at least a part of the wiring(s) included in the circuit unit 31E and moisture. Further, Embodiment 5 of the present invention allows for an easier and economically efficient production, in the same manner as Embodiment 4.

Embodiment 6

The wireless communication device included in the moisture detection system according to Embodiment 6 of the present invention has the same configuration as that of Embodiment 5. Embodiment 6 of the present invention is different from Embodiment 5 in that the wirings W3 and W4 in the memory 40B contain electrically conductive particles and a water-soluble resin.

Examples of the electrically conductive particles include particles of (Au), silver (Ag), copper (Cu), nickel (Ni), tin (Sn), bismuth (Bi), lead (Pb), zinc (Zn), palladium (Pd), platinum (Pt), aluminum (Al), tungsten (W), molybdenum (Mo) and carbon (C). In particular, the electrically conductive particles containing at least one element selected from the group consisting of gold, silver, copper, nickel, tin, bismuth, lead, zinc, palladium, platinum, aluminum and carbon, are preferred.

Examples of the water-soluble resin include homopolymers of polyethylene glycol, polyvinylpyrrolidone, polyvinyl alcohol, polyacrylamide, sodium polyacrylate, polyacrylic acid, polymethyl acrylate, polyethyl acrylate, poly-2-acrylamide-2-methylpropanesulfonic acid, sodium polystyrene sulfonate, polystyrene sulfonic acid, polyvinyl sulfonic acid, polyallylamine, polyethyleneimine and the like; and copolymers containing these components. Examples also include methyl cellulose, carboxymethyl cellulose, hydroxymethyl cellulose and casein. Further, the water-soluble resin may also be, for example, a water-soluble polyester or a water-soluble polyurethane to which a hydrophilic group such as a carboxyl group or a sulfone group is introduced.

When the wirings W3 and W4 having the above described configuration come into contact with moisture, the water-soluble resin contained therein is dissolved to cause changes in the composition of the wirings, resulting in an increase in the electrical resistance. This causes changes in the 1-bit information to be read by the control circuit 39 from the memory 40B, in the same manner as in Embodiment 4. In cases where the 1-bit information included in the signal received from the wireless communication device according to Embodiment 6 of the present invention is different from that in the normal state, the transceiver 2 detects that moisture has attached to the wireless communication device according to Embodiment 6 of the present invention.

According to Embodiment 6 of the present invention described above, it is possible to accurately detect the generation of moisture with a simple configuration, in the same manner as in Embodiment 4. Further, Embodiment 6 of the present invention allows for an easier and economically efficient production, in the same manner as Embodiment 4.

Embodiment 7

The wireless communication device included in the moisture detection system according to Embodiment 7 of the present invention has the same configuration as that of Embodiment 5. Embodiment 7 of the present invention is different from Embodiment 5 in that the wirings W3 and W4 in the memory 40B contain electrically conductive particles and a water-absorbent resin. Of these, the electrically conductive particles are formed using the same materials as those described in Embodiment 6.

Examples of the water-absorbent resin include: a water-absorbent resin obtained by polymerization of starch or cellulose, a water-soluble monomer containing a hydrophilic group such as a carboxyl group or a sulfone group and/or a monomer which becomes water-soluble by hydrolysis, and a crosslinking agent, as essential components, and carrying out hydrolysis as required; a hydrolyzate of a starch-acrylonitrile graft polymer; a hydrolyzate of a starch-acrylic acid graft polymer; a hydrolyzate of a cellulose-acrylonitrile graft polymer; a cross-linked product of carboxymethyl cellulose; a partial hydrolyzate of a cross-linked polyacrylamide; a cross-linked acrylic acid-acrylamide copolymer; a cross-linked sulfonated polystyrene; a saponified product of a vinyl ester-unsaturated carboxylic acid copolymer; a cross-linked polyacrylic acid (salt) such as sodium polyacrylate; a cross-linked acrylic acid-acrylic acid ester copolymer; an isobutylene-maleic anhydride copolymer; a cross-linked isobutylene-maleic anhydride copolymer such as sodium salt-cross-linked maleic anhydride; a cross-linked carboxylic acid-modified polyvinyl alcohol; a self-crosslinked polyacrylic acid salt; a cross-linked vinyl acetate-acrylic acid ester copolymer; and a nonionic polyalkylene oxide. The water-absorbent resin is not particularly limited, and conventionally known water-absorbent resins other than those mentioned above can also be used.

When the wirings W3 and W4 having the above described configuration come into contact with moisture, the water-absorbent resin contained therein absorbs water to cause the wirings W3 and W4 to swell. This causes an increase in the distance between the electrically conductive particles, leading to a substantial disconnection of the wirings and an increase in the resistance. This results in changes in the information to be read by the control circuit 39 from memory 40, in the same manner as in Embodiment 1. In cases where the 1-bit information included in the signal received from the wireless communication device 3 is different from that in the normal state, the transceiver 2 detects that moisture has attached to the wireless communication device 3.

According to Embodiment 7 of the present invention described above, it is possible to accurately detect the generation of moisture with a simple configuration, in the same manner as in Embodiment 5. Further, Embodiment 7 of the present invention allows for an easier and economically efficient production, in the same manner as Embodiment 5.

Embodiment 8

The wireless communication device according to Embodiment 8 of the present invention has the same configuration as that of the wireless communication device according to Embodiment 5. Embodiment 8 of the present invention is different from Embodiment 5 in that the insulating layer 55 of the memory element 50B further contains, as a photosensitive organic component, an addition reaction product of a radically polymerizable compound, and that the wirings W3 and W4 are formed using an electrically conductive material.

The radically polymerizable compound refers to a compound which contains a plurality of ethylenically unsaturated double bonds within the molecule. By the irradiation of ultraviolet (UV) light, radicals generated from a photopolymerization initiator to be described later causes the radical polymerization of the radically polymerizable compound to proceed. This leads to an improvement in the crosslinking density of the insulating layer 55, as a result of which the hardness of the insulating layer 55 can be improved.

The radically polymerizable compound is preferably a compound having a (meth)acrylic group, in which radical polymerization more easily proceeds. From the viewpoint of improving the sensitivity during the irradiation of UV light and improving the hardness of the insulating layer 55, a compound containing two or more (meth)acrylic groups within the molecule is more preferred.

From the viewpoint of improving the sensitivity during the irradiation of UV light and improving the crack resistance of the resulting cured film, the radically polymerizable compound is preferably trimethylolpropane tri(meth)acrylate, ditrimethylolpropane tetra(meth)acrylate, pentaerythritol tetra(meth)acrylate, dipentaerythritol penta(meth)acrylate, dipentaerythritol hexa(meth)acrylate, tripentaerythritol octa(meth)acrylate, 1,3,5-tris((meth)acryloxyethyl)isocyanuric acid or 9,9-bis [4-(2-(meth)acryloxyethoxy)phenyl]fluorene; or an acid-modified product thereof. Further, the radically polymerizable compound is also preferably an ethylene oxide-modified product or a propylene oxide-modified product, from the viewpoint of improving the sensitivity during the irradiation of UV light and improving the crack resistance of the resulting cured film.

The insulating layer 55 may further contain, as a photosensitive organic component, a compound (hereinafter, referred to as "photopolymerization initiator") which undergoes bond cleavage and/or a reaction due to the irradiation of UV light, and generate radicals. The incorporation of the photopolymerization initiator allows the radical polymerization of the above described radically polymerizable compound to proceed, thereby enabling to facilitate the addition reaction during the irradiation of UV light. For example, the photopolymerization initiator is preferably a benzyl ketal-based photopolymerization initiator, an α-hydroxyketone-based photopolymerization initiator, an α-aminoketone-based photopolymerization initiator, an acylphosphine oxide-based photopolymerization initiator, an oxime ester-based photopolymerization initiator, an acridine-based photopolymerization initiator, a titanocene-based photopolymerization initiator, a benzophenone-based photopolymerization initiator, an acetophenone-based photopolymerization initiator, an aromatic ketoester-based photopolymerization initiator or a benzoic acid ester-based photopolymerization initiator. From the viewpoint of improving the sensitivity during the irradiation of UV light, the photopolymerization initiator is more preferably an α-hydroxyketone-based photopolymerization initiator, an α-aminoketone-based photopolymerization initiator, an acylphosphine oxide-based photopolymerization initiator, an oxime ester-based photopolymerization initiator, an acridine-based photopolymerization initiator or a benzophenone-based photopolymerization initiator. The photopolymerization initiator is still more preferably an α-aminoketone-based photopolymerization initiator, an acylphosphine oxide-based photopolymerization initiator, or an oxime ester-based photopolymerization initiator. Specific examples of the photopolymerization initiator include 1-[4-(phenylthio)phenyl]octane-1,2-dione-2-(O-benzoyl)oxime and 1-[9-ethyl-6-(2-methylbenzoyl)-9H-carbazol-3-yl]ethanone-1-(O-acetyl)oxime, which are oxime ester-based photopolymerization initiators. However, other known materials can also be used.

The insulating layer 55 may further contain, as a photosensitive organic component, a compound (hereinafter, referred to as "photoacid generator") which generates an acid when irradiated with light. Examples of the photoacid generator include an onium salt compound, a halogen-containing compound, a diazoketone compound, a diazomethane compound, a sulfone compound, a sulfonic acid ester compound and a sulfonimide compound. Specific examples of the diazoketone compound include a 1,3-diketo-2-diazo compound, a diazobenzoquinone compound, and a diazonaphthoquinone compound. Among these, a diazonaphthoquinone compound is preferred, from the viewpoint of improving the patterning accuracy and improving the crack resistance of the insulating layer 55. Examples of preferred diazoketone compounds include an ester of 1,2-naphthoquinonediazide-4-sulfonic acid with 2,2,3,4,4'-pentahydroxybenzophenone, and an ester of 1,2-naphthoquinonediazide-4-sulfonic acid with 1,1,1-tris(4-hydroxyphenyl)ethane.

The photopolymerization initiator and the photoacid generator are preferably used in combination with a sensitizer, which is a photosensitive organic component. The sensitizer does not cause coloration in a photobleaching reaction, and thus is capable of achieving a higher sensitivity while retaining a high transparency, even in the insulating layer 55. The sensitizer is not particularly limited, and a known material can be used. However, a 9,10-disubstituted anthracene compound is particularly preferred.

The insulating layer 55 may further contain, as a photosensitive organic component, an addition reaction product of a chain transfer agent. The chain transfer agent refers to a compound capable of receiving a radical from the growth terminal of a polymer chain which is obtained by radical polymerization during the irradiation of UV light, and mediating the transfer of the radical to another polymer chain. The incorporation of a chain transfer agent enables to improve the sensitivity during the irradiation of UV light. This is assumed to be because radicals generated by the irradiation of UV light are transferred to other polymer chains by the chain transfer agent, as a result of which radical cross-linking extends deeply into the film. The chain transfer agent is preferably a thiol-based chain transfer agent.

The insulating layer 55 may further contain, as a photosensitive organic component, a polymerization inhibitor. The polymerization inhibitor refers to a compound capable of capturing a radical generated during the irradiation of UV light, or a radical at the growth terminal of a polymer chain which is obtained by radical polymerization during the irradiation of UV light, and retaining the radical as a stabilized radical, thereby terminating the radical polymerization. The incorporation of an adequate amount of polymerization inhibitor enables to prevent the generation of an excessive amount of radicals during the irradiation of UV light, and to control the radical polymerization. The polymerization inhibitor is preferably a phenol-based polymerization inhibitor.

The insulating layer 55 may further contain, in addition to a polymer to which inorganic particles are bound, inorganic particles to which no polymer is bound. Preferred materials and shape of the inorganic particles to which no polymer is bound, are the same as those of the case in which a polymer is bound, as described above.

If necessary, the insulating layer 55 may contain a viscosity modifier, a surfactant, a stabilizer, and/or the like. Further, the insulating layer 55 may contain a residual solvent. Examples of the surfactant include a fluorochemical surfactant, a silicone-based surfactant, a polyalkylene oxide-based surfactant, and an acrylic surfactant. Specific examples of the fluorochemical surfactant include MEGAFACE F142D, MEGAFACE F172, MEGAFACE F173 and MEGAFACE F183 (all of the above manufactured by DIC Corporation); and NBX-15, FTX-218 and DFX-18 (manufactured by NEOS Company Limited). Specific examples of the silicone-based surfactant include BYK-333 (manufactured by BYK Japan KK).

In Embodiment 8 of the present invention, the memory element 50B is formed using a thin film transistor including the insulating layer 55 containing a photosensitive organic matter, and this makes it possible to selectively form vias by photolithography. Therefore, for example, when vias are selectively formed in the regions of the insulating layer 55 at which the wirings W3 and W4 come into contact, and a film composed of a water-soluble resin (water-soluble resin film) is formed in each of the vias by a coating method, such as an ink jet method or a dispenser method, one or both of the water-soluble resin films dissolve upon coming into contact with moisture. This causes the disconnection of the wiring(s) which is/are in contact with the corresponding water-soluble resin film(s), resulting in an increase in the resistance. It is also possible to form a film composed of a water-absorbent resin (water-absorbent resin film), instead of the water-soluble resin film, in each of the vias in the insulating layer 55, by a coating method in the same manner as described above. In this case, when one or both of the water-absorbent resin films come into contact with moisture, the water-absorbent resin film(s) swell(s), and this causes the disconnection of the wiring(s) which is/are in contact with the corresponding water-absorbent resin film(s).

According to Embodiment 8 of the present invention described above, it is possible to accurately detect the generation of moisture with a simple configuration, in the same manner as in Embodiment 5. Further, Embodiment 8 of the present invention allows for an easier and economically efficient production, in the same manner as Embodiment 5.

Other Embodiments

Embodiments for carrying out the present invention have been described above, but the present invention is in no way limited to the above described embodiments. For example, a plurality of the wireless communication devices may be provided to a diaper. Specifically, since there is a difference between men and women in the location which is more likely to get wet at the time of urination, the wireless communication devices may be provided to all possible locations at which urine can be released. This arrangement enables to accurately detect the presence of moisture, regardless of the gender of a person using the diaper, and to provide a highly versatile diaper.

Further, the circuit unit may include one control circuit, and a plurality of memories provided at different locations. Even in this case, only one antenna is required. This configuration also allows for obtaining the same effect as the effect obtained in the case of providing a plurality of wireless communication devices, with a simpler configuration.

It is also possible to use an element formed using one or more materials selected from the group consisting of carbon nanotubes, graphene, fullerene and organic semiconductors, in an active-type wireless communication device including a built-in battery.

Further, the wireless communication device may have a circuit configuration in which the wireless communication device does not return a signal to the transceiver, when the wireless communication device comes into contact with moisture.

The communication between the transceiver and the wireless communication device may be achieved by NFC communication (near field communication) at a frequency of 13.56 MHz. In this case, for example, the wireless communication device can be installed to a bed sheet or the like, so as to detect the presence of moisture.

The wireless communication device can also be used as a moisture detection system, in a system for: checking the waterproof performance of the interior of automobiles during the production thereof, detecting water leaks during the construction of tunnels, detecting water leaks in drain pipes, or the like.

As described above, the present invention can include various types of embodiments and the like, which have not been described herein.

REFERENCE SIGNS LIST 1 moisture detection system
2 transceiver
3, 3A, 3B, 3C, 3D, 3E wireless communication device
4 diaper
31, 31A, 31B, 31C, 31D, 31E circuit unit
32 antenna
33, 37 diode
34, 36 variable capacity diode
35 voltage controlled oscillator
38 ring oscillator
39 control circuit
40, 40A memory
41 surface material
42 water absorbent material
43 waterproof material
50, 50a, 50b, 50B memory element
51, 51a, 51b source
52, 52a, 52b gate
53, 53a, 53b drain
54, 54a, 54b substrate
55, 55a, 55b insulating layer
56, 56a, 56b semiconductor layer
57 second insulating layer
BL, BL1, BL2 bit line
W1, W2, W3, W4, W11, W12, W21, W22 wiring
WL word line

The invention claimed is:

1. A wireless communication device comprising: a circuit unit; and an antenna which is connected to said circuit unit and which transmits and receives signals to and from a transceiver in a non-contact manner;

wherein said circuit unit comprises a diode; and wherein, when said diode comes into direct contact with moisture, an electrical property of the diode changes which causes said wireless communication device to transmit to said transceiver, a signal different from the signal to be transmitted when said diode is not in contact with moisture.

2. The wireless communication device according to claim 1, wherein said circuit unit comprises an element formed using one or more materials selected from the group consisting of carbon nanotubes, graphene, fullerene and organic semiconductors, and wherein the properties of said element change due to contact with moisture.

3. The wireless communication device according to claim 2, wherein at least one parameter of the signal returned in response to the signal received from said transceiver changes, when the properties of said element change.

4. The wireless communication device according to claim 1,
wherein said diode is a variable capacity diode; and
wherein, when said variable capacity diode comes into contact with moisture, said wireless communication device transmits to said transceiver, a signal having an intensity different from the intensity of the signal to be transmitted when said variable capacity diode is not in contact with moisture.

5. The wireless communication device according to claim 1,
wherein said circuit unit further comprises an oscillator circuit; and
wherein, when said diode comes into contact with moisture, said wireless communication device transmits to said transceiver, a signal having a frequency different from the frequency of the signal to be transmitted when said diode is not in contact with moisture.

6. A wireless communication device comprising:
a circuit unit; and an antenna which is connected to said circuit unit and which transmits and receives signals to and from a transceiver in a non-contact manner;
wherein said circuit unit comprises a ring oscillator; and
wherein, when said ring oscillator comes into direct contact with moisture, an electrical property of the ring oscillator changes which causes said wireless communication device to transmit to said transceiver, a signal having a frequency different from the frequency of the signal to be transmitted when said ring oscillator is not in contact with moisture.

7. A wireless communication device comprising:
a circuit unit; and an antenna which is connected to said circuit unit and which transmits and receives signals to and from a transceiver in a non-contact manner;
wherein said circuit unit comprises a memory element; and
wherein, when said memory element comes into direct contact with moisture, an electrical property of the memory element changes which causes said wireless communication device to transmit to said transceiver, a signal different from the signal to be transmitted when said memory element is not in contact with moisture.

8. The wireless communication device according to claim 2, wherein said element is formed using a carbon nanotube.

9. The wireless communication device according to claim 2, wherein a semiconductor layer included in said element is formed using a carbon nanotube.

10. A wireless communication device comprising:
a circuit unit; and an antenna which is connected to said circuit unit and which transmits and receives signals to and from a transceiver in a non-contact manner, wherein said circuit unit comprises a digital circuit; and
wherein, when at least a part of wiring of said digital circuit comes into direct contact with moisture, properties of said digital circuit change which causes wireless communication device to transmit to said transceiver, a signal including information different from the information included in the signal to be transmitted when at least a part of said wiring is not in contact with moisture.

11. The wireless communication device according to claim 10, wherein the electrical resistance of said wiring changes, when at least a part of said wiring comes into contact with moisture.

12. The wireless communication device according to claim 10, wherein at least a part of said wiring comprises electrically conductive particles and a water-soluble resin.

13. The wireless communication device according to claim 10, wherein at least a part of said wiring comprises a water-soluble electrically conductive polymer.

14. The wireless communication device according to claim 10, wherein at least a part of said wiring comprises electrically conductive particles and a water-absorbent resin.

15. A wireless communication device comprising: a circuit unit and an antenna which is connected to said circuit unit and which transmits and receives signals to and from a transceiver in a non-contact manner,
wherein said circuit unit comprises:
a wiring;
a memory element which is connected to said wiring and which stores predetermined information; and
a control circuit which reads information from said memory element and transmits the information to said transceiver;
wherein, when the wiring connected to the memory element comes into direct contact with moisture, the wiring electrical resistance changes which causes changes in the information to be read by the control circuit from the memory element; and
wherein said wireless communication device transmits signals including different information to said transceiver, depending on the presence or absence of contact between the wiring which is connected to the memory element and moisture.

16. A wireless communication device comprising: a circuit unit; and an antenna which is connected to said circuit unit and which transmits and receives signals to and from a transceiver in a non-contact manner,
wherein said circuit unit comprises:
a wiring;
a plurality of memory elements arranged in the form of an array, the plurality of memory elements being connected to said wiring; and
a control circuit which reads information from said plurality of memory elements and transmits the information to said transceiver;
wherein, when the wiring connected to the plurality of memory elements comes into direct contact with moisture, properties of the circuit unit change which causes changes in the information to be read by the control circuit from the plurality of memory elements; and
wherein said wireless communication device transmits signals including different information to said transceiver, depending on the presence or absence of contact between the wiring which is connected to the plurality of memory elements and moisture.

17. A diaper comprising:
a water absorbent material which absorbs and retains moisture; and
a waterproof material having a waterproof function and covering said water absorbent material;
wherein said diaper is capable of being attached to a human body and absorbing moisture released from the human body; and
wherein said diaper comprises the wireless communication device according to claim 1.

18. A moisture detection system, comprising:
the wireless communication device according to claim 1; and
a transceiver which is capable of communicating with said wireless communication device in a non-contact manner, and which detects the presence or absence of contact between said wireless communication device with moisture, based on the signal returned in response to the signal transmitted to said wireless communication device.

19. The wireless communication device according to claim 6, wherein said circuit unit comprises an element formed using one or more materials selected from the group consisting of carbon nanotubes, graphene, fullerene and organic semiconductors, and wherein the properties of said element change due to contact with moisture.

20. The wireless communication device according to claim 6, wherein at least one parameter of the signal returned in response to the signal received from said transceiver changes, when the properties of said element change.

21. The wireless communication device according to claim 7, wherein said circuit unit comprises an element formed using one or more materials selected from the group consisting of carbon nanotubes, graphene, fullerene and organic semiconductors, and wherein the properties of said element change due to contact with moisture.

22. The wireless communication device according to claim 7, wherein at least one parameter of the signal returned in response to the signal received from said transceiver changes, when the properties of said element change.

* * * * *